US008852613B2

(12) United States Patent
Ohnesorge et al.

(10) Patent No.: US 8,852,613 B2
(45) Date of Patent: Oct. 7, 2014

(54) **ONE DOSE VACCINATION AGAINST *MYCOPLASMA* INFECTIONS OF PIGS**

(71) Applicants: William Charles Ohnesorge, Saint Joseph, MO (US); Isabelle Freiin von Richthofen, Charlottenlund (DK); Marika Christine Genzow, Wiesbaden (DE); Martina von Freyburg, Mainz (DE); Carola Kissel, Kansas City, MO (US); Luc-Etienne Fabry, Bingen (DE); Knut Elbers, Mittelbiberach (DE); Kathleen Kwan Young Park, St. Joseph, MO (US)

(72) Inventors: William Charles Ohnesorge, Saint Joseph, MO (US); Isabelle Freiin von Richthofen, Charlottenlund (DK); Marika Christine Genzow, Wiesbaden (DE); Martina von Freyburg, Mainz (DE); Carola Kissel, Kansas City, MO (US); Luc-Etienne Fabry, Bingen (DE); Knut Elbers, Mittelbiberach (DE); Kathleen Kwan Young Park, St. Joseph, MO (US)

(73) Assignee: Boehringer Ingelheim Vetmedica, Inc., St. Joseph, MI (US)

( * ) Notice: Subject to any disclaimer, the term of this patent is extended or adjusted under 35 U.S.C. 154(b) by 0 days.

(21) Appl. No.: 13/869,574

(22) Filed: Apr. 24, 2013

(65) Prior Publication Data

US 2013/0230558 A1 Sep. 5, 2013

Related U.S. Application Data

(62) Division of application No. 12/423,658, filed on Apr. 14, 2009, now Pat. No. 8,444,989.

(60) Provisional application No. 61/046,244, filed on Apr. 18, 2008.

(51) Int. Cl.
| | |
|---|---|
| *A61K 39/02* | (2006.01) |
| *A61K 39/40* | (2006.01) |
| *C12R 1/35* | (2006.01) |
| *C12N 1/20* | (2006.01) |
| *A61K 39/00* | (2006.01) |

(52) U.S. Cl.
CPC ............ *A61K 39/0241* (2013.01); *A61K 39/40* (2013.01); *C12R 1/35* (2013.01); *C12N 1/20* (2013.01); *A61K 2039/552* (2013.01); *A61K 2039/521* (2013.01)
USPC ..................................................... 424/264.1

(58) Field of Classification Search
CPC ....................................................... A61K 39/02
USPC ........................................................ 424/264.1
See application file for complete search history.

(56) References Cited

U.S. PATENT DOCUMENTS

| | | | | |
|---|---|---|---|---|
| 5,565,205 | A * | 10/1996 | Petersen et al. | ............ 424/264.1 |
| 7,109,025 | B1 * | 9/2006 | Eloit et al. | ................ 435/320.1 |
| 7,914,992 | B2 * | 3/2011 | Fachinger et al. | ............. 514/3.7 |
| 8,119,143 | B2 * | 2/2012 | Roof et al. | ................ 424/204.1 |
| RE44,399 | E * | 7/2013 | Keich et al. | .................... 424/9.1 |
| 2003/0017171 | A1 * | 1/2003 | Chu et al. | .................. 424/201.1 |
| 2003/0064079 | A1 * | 4/2003 | Goudie et al. | ............. 424/248.1 |
| 2006/0233830 | A1 * | 10/2006 | Wong et al. | ................ 424/204.1 |
| 2014/0056940 | A1 * | 2/2014 | Dominowski et al. | ..... 424/209.1 |

FOREIGN PATENT DOCUMENTS

| | | |
|---|---|---|
| WO | 9203157 A1 | 3/1992 |
| WO | 0249666 A2 | 6/2002 |

OTHER PUBLICATIONS

"Carbomer". PharmEuropa, vol. 8, No. 2, Jun. 1996, pp. 221-223.
Dawson et al., "Studies of the field efficacy and safety of a single-dose *Mycoplasma hyopneumoniae* vaccine for pigs". Veterinary Record, vol. 151, 2002, pp. 535-538.
Kolb et al., "Performance of conventional health pigs vaccinated with Ingelvac MycoFLEX® or Suvaxyn® RespiFend". Sep. 2008, Allan D. Leman Swine Conference 2008, University of Minnesota, Minnesota, p. 27.
Maes et al., "Effect of vaccination against *Mycoplasma hyopneumoniae* in pig herds with an all-in/all-out production system". Vaccine, vol. 17, 1999, pp. 1024-1034.
Ross et al., "Characteristics of protective activity of *Mycoplasma hyopneumoniae* vaccine" Oct. 1984, American Journal of Veterinary Research, vol. 45, No. 10, pp. 1899-1905.
Thacker, Eileen L., "Mycoplasmal Diseases". Diseases of Swine, 9th Edition, Ch. 42, 2006, pp. 701-717.

* cited by examiner

*Primary Examiner* — Albert Navarro
*Assistant Examiner* — Ginny Portner
(74) *Attorney, Agent, or Firm* — Michael P. Morris; Wendy M. Gombert

(57) ABSTRACT

The present invention provides a one phase, aqueous vaccine composition for immunizing an animal against infection by *Mycoplasma hyopneumoniae*, comprising: an immunizing amount of a *Mycoplasma hyopneumoniae* bacterin, an acrylic acid polymer in the concentration range between 0.8 and 1.2 mg/ml, and a pharmaceutically acceptable carrier, and substantially no oil. It is especially useful for immunizing a pig against infection by *Mycoplasma hyopneumoniae* for at least 20 weeks after a single administration, which effective immunity is reached within 4 weeks after vaccination.

5 Claims, No Drawings

ONE DOSE VACCINATION AGAINST *MYCOPLASMA* INFECTIONS OF PIGS

FIELD OF THE INVENTION

The present invention relates to vaccine compositions designed to immunize an animal effectively against an infection by *Mycoplasma hyopneumoniae* (*M. hyopneumoniae*), especially to respective one phase, aqueous vaccine compositions for immunizing pigs.

BACKGROUND OF THE INVENTION

*M. hyopneumoniae* is the primary pathogen of enzootic pneumonia, an economically important and globally, highly prevalent disease in pigs. *M. hyopneumoniae* is also considered to be one of the primary agents involved in the porcine respiratory disease complex (PRDC; see E. L. Thacker; 2006; Diseases of Swine; 9$^{th}$ edition; Blackwell publishing; editor: B. E. straw et al.; pages 701-717). Mycoplasmal pneumonia is most commonly spread through direct contact with respiratory tract secretions of infected swine, but may also be spread through airborne transmission. Clinically, mycoplasmal pneumonia can be described as a chronic disease with high morbidity and low mortality. The principal sign is a chronic nonproductive cough, with inappetence, labored breathing (thumping), and unthriftiness, or an unhealthy appearance.

Despite the low mortality of enzootic pneumonia due to infection with *M. hyopneumoniae*, this disease is a significant economic problem for swine producers worldwide. An approximate herd average lung lesion score of 10 depresses growth rate by 5% (37.5 g/day) (see Burch; 2007; Cost of Disease—Enzootic Pneumonia; *Pig World*, February 2007). Additionally, a herd average lung lesion score of 10 reduces the Feed Conversion Rate by about 4.5% (see Straw B. E., et al.; 1986; Examination of Swine at Slaughter. Part II. Findings at Slaughter and their Significance). Consequently, prevention of this disease would provide significant commercial benefit to swine husbandry (see e.g. Maes et al.; 1999; *Vaccine*, vol. 17, pages 1024-1034).

At present, commercial vaccines to protect healthy swine against the clinical signs caused by *M. hyopneumoniae* are the major tools for reducing the clinical impact of the disease. Most commercial vaccines consist of adjuvanted whole cell preparations. Commercial vaccines differ significantly in respect to their administration regime. International application WO 92/03157 A1, for example, discloses a vaccine against infections by *M. hyopneumoniae* that comprises a binary ethyleneimine (BEI) inactivated *M. hyopneumoniae* strain and 0.2% (w/v) (i.e. 2 mg/ml) acrylic acid.

Over the past few years single-dose vaccines have been developed which allow a "one shot" immunization to reach an acceptable level of immunity against the respective infection. Additionally, technical progress has been made with respect to the apparatus used in the vaccination step itself. For example, US 2008/0014221 A1 discloses an immunization method against *M. hyopneumoniae* infections that administers a single dose vaccine with a liquid, jet, needle-free injector.

An example for the development of single-dose vaccines can be seen in the publication "Studies of the field efficacy and safety of a single-dose *Mycoplasma hyopneumoniae* vaccine for pigs" (2002) by A. Dawson, et al., *Veterinary Record*, vol. 151, pages 535-538. It describes a field study of three- to five-week-old pigs, immunized once by a whole cell vaccine of *M. hyopneumoniae* comprising the AMPHIGEN® adjuvant from Pfizer (New York, USA), in comparison to a control group being immunized with physiological saline solution. According to the manufacturer's information (see "Next generation adjuvant system: Key to enhanced protection conferred by BVDV (Types 1 and 2) components of CATTLEMASTER®GOLD™" adjuvant; Pfizer Animal Health, *Technical Bulletin*, July 2004, page 4), the AMPHIGEN® adjuvant is a composition of a lecithin-derived phospholipid and a glycolipid surfactant in a light, highly refined oil.

The disadvantages of an oily adjuvant (e.g. adverse local reactions such as lumps, abscesses, and granulomas at the injection site) are overcome in AMPHIGEN® adjuvant by the addition of lecithin, which "naturalizes" the oil and makes it more accessible to the cells of the immune system. Aluminum hydroxide, a commonly used adjuvant in vaccines, and conventional oil adjuvants lack this compatibility. Additionally, because of its low viscosity, AMPHIGEN® adjuvant makes the respective vaccine highly syringeable and minimizes reactions upon injection. In comparison, water-in-oil based vaccines are, due to their high viscosity, extremely difficult to draw up into a syringe and are additionally often associated with long-lasting reactions at the site where the products are administered. In the two described Dawson studies, the volume of the vaccine was 2 ml, comprising the antigen and the adjuvant or the saline, respectively. As a result, the vaccinated animals had significantly lower lung lesion scores than the control animals (P=0.0022 and in a parallel group P=0.0056).

A further development, produced by the same manufacturer, available under the trade name RESPISURE-ONE® adjuvant (see pfizerah.com/product_overview; printed Apr. 10, 2008) also comprises a whole cell bacterin of *M. hyopneumoniae* and the oil-in-water adjuvant AMPHIGEN®. This bacterin is described as able to elicit 25 weeks of immunization after administering a single dose and as being effective in pigs one week of age or older. But, the total volume of the applied dose of 2 ml is still not optimal. Smaller volumes would be advantageous. Further, the viscosity of this vaccine—though ameliorated in comparison to other oil comprising adjuvants—still needs to be improved.

Another route to enhance the immunogenicity of an antigen by the admixture of an adjuvant preparation has been chosen by Wyeth/Fort Dodge Animal Health (FDAH; Madison, N.J., USA). Fort Dodge markets a *M. hyopneumoniae* bacterin under the trade name SUVAXYN RESPIFEND® MH for use as a vaccine. This vaccine contains 2 mg/ml CARBOPOL® carbomer as an adjuvant and is recommended as a two-dose vaccine for pigs at least one-week old, with the second dose to be administered two to three weeks after the first vaccination. But, a two-dose vaccine has the obvious disadvantage of requiring a second handling of the animals in order to provide full protection against disease.

A further development designed for a single administration is disclosed in the international application WO 02/49666 A2 that is based on U.S. application 60/256,637. The disclosed *M. hyopneumoniae* vaccine comprises an adjuvant mixture comprising an acrylic acid polymer and a mixture of a metabolizable oil and a polyoxyethylene-polypropylene block copolymer. This special admixture of a certain oil with the mentioned other ingredients is described as enhancing the immunogenicity of the bacterin so as to elicit protective immunity after a single dose of the vaccine. It is explicitly disclosed that the acrylic acid polymer is a carboxymethylene polymer, esp. CARBOPOL® 934P (Carbamer 934P) carbomer which may be present in the amount of about 2 ml/l. Such acrylic acid polymers were formerly marketed by B. F. Goodrich, now Noveon, Inc. (Pedricktown, N.J., USA) as CARBOPOL® 934 P NF and 941 NF carbomers. They are polymers of acrylic acid cross-linked with polyallylsucrose and have the chemical formula $(CH_2CHOOOH)_n$. These polymers form aqueous gels which suitably formulate with aqueous carriers. In explicitly disclosed modes the metabolizable oil is squalene or squalane, and the polyoxyethylene-polypropylene block copolymers are the nonionic surfactants marketed by BASF (Ludwigshafen, Germany) as PLURONIC® E L121, L61, L, 81 or L101 nonionic surfactants. Such vaccines elicit four months duration of immunity (DoI) in pigs induced by one-dose vaccination of the respective vaccine at an age of three weeks. These vaccines comprise a significant portion of oil and are applied at total volumes of 2 ml.

There remains a need to develop a vaccine against the swine pathogen M. hyopneumoniae that reduces the clinical signs of enzootic pneumonia and allows a long term effective immunity after a single administration of the vaccine, combined with an early onset of effective immunity. The design of the composition should avoid the negative side effects that accompanied oil adjuvanted vaccines, especially an undesirable high viscosity and local reactions at the injection site. Such a vaccine should additionally have the capacity to be effectively applied in doses less than 2 ml, preferably not more than 1 ml, to elicit effective immunity.

SUMMARY OF THE INVENTION

The present invention provides a one phase, aqueous vaccine composition for immunizing an animal against infection by Mycoplasma hyopneumoniae, comprising:
an immunizing amount of a Mycoplasma hyopneumoniae bacterin,
an acrylic acid polymer in the concentration range between 0.8 and 1.2 mg/ml,
and a pharmaceutically acceptable carrier, and substantially no oil.

In a preferred mode it provides a one phase, aqueous vaccine composition for immunizing an animal against infection by Mycoplasma hyopneumoniae, consisting of:
an immunizing amount of a Mycoplasma hyopneumoniae bacterin,
an acrylic acid polymer in the concentration range between 0.8 and 1.2 mg/ml,
and a pharmaceutically acceptable carrier, and substantially no other ingredients.

Further aspects of the present invention pertain to:
the use of a one phase aqueous vaccine composition according to the invention to immunize an animal to elicit effective immunity against M. hyopneumoniae;
the use of the substantially pure components mentioned above to prepare a one phase, aqueous vaccine composition that confers effective immunity to an animal against infection by M. hyopneumoniae; and
a method for prevention against and/or reducing the clinical signs caused by M. hyopneumoniae and/or for reducing the overall bacterial load of M. hyopneumoniae in an animal or group of animals, comprising administering to said animal(s) a one phase, aqueous vaccine composition according to the invention.

Preferred embodiments will be described in detail below.

DETAILED DESCRIPTION

Unless otherwise defined, all technical and scientific terms used herein have the same meaning as those commonly understood by one of ordinary skill in the art to which the invention pertains. Generally, the procedures for cell culture, infection, protein purification, molecular biology methods and the like are common methods used in the art.

All values and concentrations presented herein are subject to inherent variations acceptable in biological science within an error of ±10%. The term "about" also refers to this acceptable variation.

As mentioned above, the present invention provides a one phase, aqueous vaccine composition for immunizing an animal against infection by Mycoplasma hyopneumoniae, comprising:
an immunizing amount of a Mycoplasma hyopneumoniae bacterin,
an acrylic acid polymer in the concentration range between 0.8 and 1.2 mg/ml,
a pharmaceutically acceptable carrier, and substantially no oil.

For purposes of the present invention "one phase" refers to a water-based solution wherein the solution is mainly comprised of liquid, which is in a single phase. For example, oil-in-water and water-in-oil emulsions would not be considered one phase since the liquid in the emulsion separates and, therefore, is in two separate phases, oil and water.

In a preferred mode it provides a one phase, aqueous vaccine composition for immunizing an animal against infection by Mycoplasma hyopneumoniae, consisting of:
an immunizing amount of a Mycoplasma hyopneumoniae bacterin,
an acrylic acid polymer in the concentration range between 0.8 and 1.2 mg/ml,
a pharmaceutically acceptable carrier, and substantially no other ingredients.

Mycoplasma hyopneumoniae is the described pathogen of enzootic pneumonia, and is most probably involved in the porcine respiratory disease complex (PRDC). It is deposited at recognized institutions, e.g. at the American Type Culture Collection, 10801 University Boulevard, Manassas, Va. 20110-2209, USA (ATCC; accessible through the World Wide Web address for atcc.org on the internet), Mycoplasma hyopneumoniae strain J is deposited under ATCC number 25934.

It is recommended to use ATCC medium 1699 (see example 1) as an appropriate growth medium for the cultivation of M. hyopneumoniae. Other working media might be developed by a person skilled in the art, especially based on the knowledge of this recipe.

A M. hyopneumoniae bacterin according to the invention can be prepared from the above-mentioned ingredients by methods known to a person skilled in the art. In brief, a typical production process can be summarized by the following steps:

(1) cultivation of M. hyopneumoniae in an appropriate medium up to an appropriate cell density (calculated e.g. via the DNA content of the culture broth); and (2) inactivation e.g. physically by heat denaturation or shear force or by an appropriate chemical agent, e.g. binary ethyleneimine (BEI) or preferably by formalin.

Such a bacterin can be fractionated and further purified before further preparation of the vaccine. Appropriate techniques are known to a person skilled in the art. For practical reasons it is preferred to use an inactivated whole cell bacterin.

The antigen amount of a vaccine composition according to the invention is dependent from and calculated based on the amount of bacteria grown in the foregoing cultivation. In a preferred embodiment the bacterial cell numbers per ml are calculated in colony forming units (cfu), i.e. living cells, which can be measured by a person skilled in the art.

It is preferred to use a bacterin with an antigen amount of at least 3 log 10 bacterial cells per ml of the fermentation broth before inactivation. Increasingly preferred are concentrations between 4 log 10 and 5 log 10, on one side, and 11 log 10, 10 log 10, 9 log 10 and 8 log 10 bacterial cells per ml of the fermentation broth before inactivation, on the other side.

Taking into account that this bacterin will be mixed with other ingredients in order to design the final vaccine composition, these bacterial cell concentrations of the broth will lead to a vaccine to which bacterial cell numbers can be ascribed to that preferably lie in respectively lower concentration ranges. Increasingly preferred are percentage values of 20, 30, 40, 50, 60, 70 and 80% (v/v) of such bacterin volume on the total amount of the fully formulated vaccine, which leads to concentration equivalents between 1.5 log 9 and 8.8 log 10 of the fully formulated vaccine composition.

*M. hyopneumoniae* is not a typical bacterium as many of its surface proteins are lipoproteins, which are less immunogenic than typical proteins found in other bacteria. Thus, an adjuvant that would produce a good immune response is desired in order to gain an optimal immune response upon vaccination.

As an appropriate adjuvant an acrylic acid polymer has been chosen and is to be applied in the concentration range between 0.8 and 1.2 mg/ml. Using such an adjuvant and avoiding the addition of an oil allows a single phase vaccine, which means that this vaccine composition is not an emulsion of oil and water, in any combination (oil-in-water, water-in-oil etc.).

Advantageous adjuvant compounds according to the invention are the polymers of acrylic acid which are cross-linked, especially with polyalkenyl ethers of sugars or polyalcohols. These compounds are known by the term carbomer (*Pharmeuropa*, Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl.

The products sold under the name CARBOPOL® carbomer (BF Goodrich, Ohio, USA; a trademark by Noveon (now: Lubrizol; Pedricktown, N.J., USA) are particularly appropriate. They are cross-linked with an allyl sucrose or with allyl pentaerythritol. Among them, there may be mentioned CARBOPOL® 974P, 934P and 971P carbomers. The use of CARBOPOL® 971P carbomer is preferred. The dissolution of these polymers in water leads to an acid solution that will be neutralized, preferably to physiological pH, to make the adjuvant solution into which the immunogenic, immunological, or vaccine composition itself will be incorporated.

An acrylic acid polymer was chosen as adjuvant for a preferred vaccine composition according to the invention, because it produces an aqueous formulation that has low viscosity in comparison to water-in-oil emulsions. Moreover, carbomer is known to minimize the risk of local reactions at the injection site.

A pharmaceutically acceptable carrier, according to invention, is an immunologically inert chemical substance, preferably a buffer and/or a (e.g. buffered) solution of an inorganic salt in water. It is used to dilute the mixture of the bacterin and the adjuvant up to an appropriate concentration.

Subsequent to the above-described two preparation steps of the bacterin, the final vaccine composition according to the invention can be prepared by the following steps: admixing of the adjuvant either separately or in parallel; admixing of the pharmaceutically acceptable carrier; and by final steps the product is bottled.

The final packaging steps allow the preparation of e.g. 1 ml doses, which are then ready for the immunization of an animal. Larger volume doses are also possible, e.g for the use in an apparatus designed for the immunization of several animals, one after another in an immunization campaign (e.g. the use of a liquid, jet, needle-free injector).

The control of the finished product advantageously includes: testing for potency in comparison to another vaccine from the state of the art or prepared as a reference, sterility, swine safety, appearance, viscosity, identity, pH, formaldehyde content, and excipients, according to the respective legal requirements. Such controls can be performed by routine experiments, known to a person skilled in the art.

One feature of the invention is that, in preferred forms, it substantially contains no other ingredients. As described, the bacterin is prepared from a fermentation culture of *M. hyopneumoniae* without further separation steps, which means that the final vaccine composition does comprise minor ingredients from the fermentation process. These are media components, which have not been used up by the bacteria and products of the bacterial metabolism. Additionally there might remain traces of antifoam substances of the inactivating agent, e.g. polymerization products from BEI or formalin and of the chemical used to neutralize the inactivating agent, e.g. sodium bisulfite. However, if any traces of oily substances remain, e.g. an antifoam substance, they are preferably below 0.01% (v/v) of the total composition and are especially not sufficient to form an oily phase in the vaccine composition which has the overall appearance of a one phase, aqueous solution.

It is preferred to package the vaccine composition according to the invention in single dose units, e.g. in vials of 1 ml which are ready to use for the immunization of a single animal or in larger bottles (up to several hundred milliliters) ready to use for the immunization of a larger number of animals in a short period of time. As a consequence, the vaccine does not need to contain any preservative. In doing so, the use of potentially toxic constituents is further reduced.

The other ingredients, e.g. commercially bought products with a purity out of the control of the manufacturer of the vaccine, are also to be seen as substantially pure in the sense of the invention. Preferably any minor traces of other ingredients are less than 2% (w/v), and increasingly more preferred of less than 1, 0.5, 0.1, 0.05 and 0.01% (w/v) and can be ignored.

A one phase, aqueous vaccine composition according to the invention can be administered to the animal to be vaccinated by any appropriate route known to a person skilled in the art. The vaccine composition provided herewith may be administered intradermally, intratracheally, orally, intranasally, intravaginally or intramuscularly. The composition is preferably administered intramuscularly.

In a preferred embodiment, a vaccine composition according to the invention elicits effective immunity beginning from 4 weeks after immunization (OoI; onset of immunity) and lasts at least for 20 weeks after immunization (DoI; duration of immunity). Increasingly more preferred are earlier onset data of about 3.5, 3, 2.5 or 2 weeks of OoI, or even earlier, on one side, and longer lasting protection data of about 21, 22, 23, 24, 25 and 26 weeks DoI or even longer, on the other side.

The advantages of a vaccine composition according to the invention with respect to the duration of effective immunity become even more evident from the examples of this application. Herein, it is disclosed that an OoI of 2 weeks and a DoI of 26 weeks can be reached by a vaccine composition according to the invention. It was not predicted that this result could be reached by a single immunization with a single dose of a comparably small volume and without the use of an oil as part of the adjuvant. Further, it was found to be advantageous to immunize the animals, esp. pigs at the age of 2 to 4 weeks, (and accordingly a large group of animals of an equal age, grown in parallel) against the onset of enzootic pneumonia as early as possible to obtain protection. It was also found to be advantageous to immunize the animals, esp. pigs at an age of more than 4 weeks of the pigs to be immunized, e.g. breeding animals, before they are re-allocated to breeder organizations.

In a preferred embodiment a one phase, aqueous vaccine composition according to the invention is characterized by the fact that the vaccine composition elicits effective immunity against *M. hyopneumoniae* after the administration of 1 ml of said one phase, aqueous vaccine composition.

According to the invention, the term "effective immunity" (or "effectively immunizes" or other variants thereof) is defined as a reduction of clinical signs (examples: see below) caused by *M. hyopneumonia* in an animal or in a group of animals as compared to a non-vaccinated control animal or group of animals, reached by vaccination with an one phase, aqueous vaccine composition according to the invention.

This effect is to be seen in the context that an infection by these bacteria leads significantly to a chronic disease with high morbidity and low mortality, i.e. to a form of enzootic pneumonia, accompanied—in economic terms—with a depression of growth rate and reduction of the feed conversion rate of a single animal, and of a herd alike. Vaccinated animals and vaccinated groups of animals show a reduced depression of growth rate and a better feed conversion rate upon infection by *M. hyopneumoniae*, in comparison to control animals, even though the vaccinated animals may not be totally free from clinical signs (see below).

According to a further embodiment, the term "effective immunity" can be defined by a reduction of the overall bacterial load in an animal vaccinated with the vaccine composition provided by the invention as compared to a non-vaccinated animal after an infection with *M. hyopneumoniae*. The bacterial load can be estimated with numbers of genome equivalents per ml fluid or per mg tissue. The bacterial load is preferably estimated from lung tissue or blood serum. Methods to estimate the genome equivalents of *M. hyopneumoniae* are well known in the art. It is common practice to extract a probe of genomic DNA of the bacteria, especially selected from non-coding regions to avoid mRNA-based effects, and to amplify a characteristic sequence by PCR. The total occurrence of this characteristic genomic sequence is then equivalent to the total cell number.

Enzootic pneumonia (EP), caused by *M. hyopneumoniae* is characterized by chronic non-productive cough, pneumonia, reduced performance in the growing-finishing pig, as well as, typical lung lesions. Factors like re-grouping or crowding of animal groups, concurrent respiratory infections, and management and environmental effects, largely effect economic losses (e.g. decreased weight gain, poor feed conversion) and severity of disease. Accordingly, the term "reduction of clinical signs" as reached by the discussed invention, means, but is not limited to, the reduction in severity or incidence of one or more of the signs selected from the group consisting of: fever, respiratory distress, labored breathing, cough, lung lesions, pneumonia, decreased appetite, growth retardation, growth variance, and weight-loss.

The term "reduction of clinical signs" also comprises a reduction of infectiosity by a single vaccinated and subsequently infected animal or group of animals, in comparison to a non-vaccinated but subsequently infected control animal or control group of animals. The risk of further *M. hyopneumoniae* infections to be spread by a vaccinated animal is expected to be lower than by a not vaccinated animal. Consequently, a further, additionally preferred mode of the invention is a one phase aqueous vaccine composition according to the invention that leads to a reduction of the rate of infectiosity of a single animal or of a group of animals in comparison to a non-vaccinated but subsequently infected control animal or control group of animals.

The terms "reduction" "reduce" and "reducing", esp. in the context of the phrases "reduction of clinical signs" as well as "reduction of the overall bacterial load" as used herein means, but is not limited to, a reduction of the severity or incidence of respective symptom(s) or bacterial load as defined herein, in an vaccinated animal or in a group of vaccinated animals of more than 10%, preferably of more than 20%, even more preferred of more than 30%, even more preferred of more than 40%, even more preferred of more than 50% even more preferred of more than 70%, even more preferred of more than 100% (2-fold) and most preferred of more than 3-fold as compared to a non-vaccinated animal or group of animals. All figures calculated for a group of animals refer to the average figures calculated for such group of animals based on the individual figures calculated for each single animal.

The following preferred embodiments of the invention are substantiated by the explanations above and/or will be further illustrated by the examples of this application.

In a preferred embodiment a one phase, aqueous vaccine composition according to the invention is characterized by the fact that the vaccine composition elicits effective immunity against *Mycoplasma hyopneumoniae* for an animal by a single administration.

In a preferred embodiment a one phase, aqueous vaccine composition according to the invention is characterized by the fact that the vaccine composition elicits effective immunity against *Mycoplasma hyopneumoniae* for pigs by a single administration, which effective immunity is reached within 4 weeks after vaccination.

In a preferred embodiment a one phase, aqueous vaccine composition according to the invention is characterized by the fact that the vaccine composition elicits effective immunity against *Mycoplasma hyopneumoniae* for pigs by a single administration, which effective immunity is reached within 2 weeks after vaccination.

In a preferred embodiment a one phase, aqueous vaccine composition according to the invention is characterized by the fact that the vaccine composition elicits effective immunity against *Mycoplasma hyopneumoniae* for pigs by a single administration, which effective immunity lasts for at least 20 weeks.

In a preferred embodiment a one phase, aqueous vaccine composition according to the invention is characterized by the fact that the vaccine composition elicits effective immunity against *Mycoplasma hyopneumoniae* for pigs by a single administration, which effective immunity lasts for at least 26 weeks.

In a preferred embodiment a one phase, aqueous vaccine composition according to the invention is characterized by the fact that the *Mycoplasma hyopneumoniae* bacterin is an inactivated whole cell bacterin.

In a preferred embodiment a one phase, aqueous vaccine composition according to the invention is characterized by the fact that the *Mycoplasma hyopneumoniae* bacterin is a whole cell *Mycoplasma hyopneumoniae* bacterin that is inactivated by formalin.

In a preferred embodiment a one phase, aqueous vaccine composition according to the invention is characterized by the fact that the *Mycoplasma hyopneumoniae* bacterin is made from strain *Mycoplasma hyopneumoniae* J (e.g. ATCC 25934).

In a preferred embodiment a one phase, aqueous vaccine composition according to the invention is characterized by the fact that the *Mycoplasma hyopneumoniae* bacterin has an antigen amount of at least 3 log 10 per ml before inactivation.

In a preferred embodiment a one phase, aqueous vaccine composition according to the invention is characterized by the fact that the *Mycoplasma hyopneumoniae* bacterin has an antigen amount between 5 log 10 and 11 log 10 per ml before inactivation.

In a preferred embodiment a one phase, aqueous vaccine composition according to the invention is characterized by the fact that the acrylic acid polymer is a carboxymethylene polymer, preferably cross-linked with polyallylsucrose.

In a preferred embodiment a one phase, aqueous vaccine composition according to the invention is characterized by the fact that the acrylic acid polymer is Carbomer, as defined above.

In a preferred embodiment a one phase, aqueous vaccine composition according to the invention is characterized by the fact that the acrylic acid polymer is in a concentration range between 0.9 and 1.1 mg/ml.

In a preferred embodiment a one phase, aqueous vaccine composition according to the invention is characterized by the fact that the acrylic acid polymer is in a concentration range between 0.95 and 1.05 mg/ml.

In a preferred embodiment a one phase, aqueous vaccine composition according to the invention is characterized by the fact that the pharmaceutically acceptable carrier is selected from a buffered or non-buffered aqueous solution of an inorganic salt.

In a preferred embodiment a one phase, aqueous vaccine composition according to the invention is characterized by the fact that the viscosity of the vaccine composition is below 9 cP (25° C.).

In a preferred embodiment a one phase, aqueous vaccine composition according to the invention is characterized by the fact that the viscosity of the vaccine composition is in the range between 6 and 8 cP (25° C.).

In a preferred embodiment a one phase, aqueous vaccine composition according to the invention is characterized by the fact that it consists of the following substantially pure constituents: a formalin-inactivated whole cell *Mycoplasma hyopneumoniae* J strain (even more preferably one deposited as ATCC 25934) bacterin, with an antigen amount between 5 log 10 and 8 log 10 per ml before inactivation; 1 mg/ml Carbomer; up to 1 ml sodium chloride solution, 0.85% (w/v) in water, and substantially no other ingredients.

Another mode to carry out the invention is the use of a one phase, aqueous vaccine composition according to the invention to immunize an animal to elicit effective immunity against *Mycoplasma hyopneumoniae*. In a preferred embodiment this mode is a use to immunize a pig to elicit effective immunity against *Mycoplasma hyopneumoniae* over a period of at least 20 weeks after a single administration, wherein said effective immunity is reached within 4 weeks after vaccination. In another preferred embodiment, this mode is a use to immunize a pig to elicit effective immunity against *Mycoplasma hyopneumoniae* over a period of at least 26 weeks after a single administration, wherein said effective immunity is reached within 2 weeks after vaccination.

Another mode to carry out the invention is the use of substantially pure *Mycoplasma hyopneumoniae* bacterin; an acrylic acid polymer in the final concentration range between 0.8 and 1.2 mg/ml; a pharmaceutically acceptable carrier; and substantially no other ingredients to prepare a one phase, aqueous vaccine composition that confers effective immunity to an animal against infection by *Mycoplasma hyopneumoniae*.

Another mode to carry out the invention is a use of substantially pure *Mycoplasma hyopneumoniae* bacterin; an acrylic acid polymer in the final concentration range between 0.8 and 1.2 mg/ml; a pharmaceutically acceptable carrier; and substantially no other ingredients to prepare a one phase, aqueous vaccine composition that confers effective immunity to a pig against infection by *Mycoplasma hyopneumoniae* over a period of at least 20 weeks after a single administration, wherein said effective immunity is reached within 4 weeks after vaccination.

Another mode to carry out the invention is a use of substantially pure *Mycoplasma hyopneumoniae* bacterin; an acrylic acid polymer in the final concentration range between 0.8 and 1.2 mg/ml; a pharmaceutically acceptable carrier; and substantially no other ingredients to prepare a one phase, aqueous vaccine composition that confers effective immunity to a pig against infection by *Mycoplasma hyopneumoniae* over a period of at least 26 weeks after a single administration, wherein said effective immunity is reached within 2 weeks after vaccination.

Another mode to carry out the invention is a method for prevention against and/or reducing the clinical signs caused by *Mycoplasma hyopneumoniae* and/or for reducing the overall bacterial load of *Mycoplasma hyopneumoniae* in an animal or group of animals, comprising administering to said animal(s) a one phase, aqueous vaccine composition according to the invention.

In a preferred embodiment such a method according to the invention is characterized by the fact that said one phase, aqueous vaccine composition is administered to the animal(s) in (a) dose(s) of 1 ml of said one phase, aqueous vaccine composition.

In a preferred embodiment such a method according to the invention is characterized by the fact that said one phase, aqueous vaccine composition is administered to the animal by a single dose.

In a preferred embodiment such a method according to the invention is characterized by the fact that said administration is effective for prevention against and/or reducing the clinical signs caused by *Mycoplasma hyopneumoniae* and/or for reducing the overall bacterial load of *Mycoplasma hyopneumoniae* in an animal or a group of animals as compared to a non-vaccinated animal or group of animals.

In a preferred embodiment such a method according to the invention is characterized by the fact that the clinical signs are selected from the group consisting of fever, respiratory distress, labored breathing, cough, lung lesions, pneumonia, decreased appetite, growth retardation, growth variance, and weight-loss.

In a preferred embodiment such a method according to the invention is characterized by the fact that said administration is effective after the administration of a single dose of said one phase, aqueous vaccine composition.

In a preferred embodiment such a method according to the invention is characterized by the fact that said administration is made at the age of 2 to 4 weeks of the pig to be immunized.

In a preferred embodiment such a method according to the invention is characterized by the fact that said administration is made at an age of more than 4 weeks of the pig to be immunized.

In a preferred embodiment such a method according to the invention is characterized by the fact that said administration is effective for prevention against and/or reducing the clinical signs caused by *Mycoplasma hyopneumoniae* and/or for reducing the overall bacterial load of *Mycoplasma hyopneumoniae* in an animal or a group of animals over a period of at least 20 weeks after said administration.

In a preferred embodiment such a method according to the invention is characterized by the fact that said administration is effective for prevention against and/or reducing the clinical signs caused by *Mycoplasma hyopneumoniae* and/or for reducing the overall bacterial load of *Mycoplasma hyopneumoniae* in an animal or a group of animals over a period of at least 26 weeks after said administration.

In a preferred embodiment such a method according to the invention is characterized by the fact that said administration is effective for prevention against and/or reducing the clinical signs caused by *Mycoplasma hyopneumoniae* and/or for reducing the overall bacterial load of *Mycoplasma hyopneumoniae* in an animal or a group of animals wherein said effective immunity is reached within 4 weeks after said administration.

In a preferred embodiment such a method according to the invention is characterized by the fact that said administration is effective for prevention against and/or reducing the clinical signs caused by *Mycoplasma hyopneumoniae* and/or for reducing the overall bacterial load of *Mycoplasma hyopneumoniae* in an animal or a group of animals wherein said effective immunity is reached within 2 weeks after said administration.

The following examples are intended to further explain the underlying invention without any limitation with respect to the scope of protection. Those of skill in the art should, in light of the present disclosure, appreciate that many changes can be made in the specific embodiments which are disclosed and still obtain a like or similar result without departing from the spirit and scope of the invention.

EXAMPLES

Example 1

Culturing of *M. hyopneumoniae*

*M. hyopneumoniae* is a fastidious aerobic bacterium that grows very slowly. It requires a complex medium supplemented with yeast extract solution and porcine serum. A strain of *M. hyopneumoniae* can be purchased from the American Type Culture Collection, 10801 University Boulevard, Manassas, Va. 20110-2209, USA (ATCC; see the World Wide Web address for atcc.org on the internet) under ATCC number 25095. Growth conditions are aerobic (dissolved oxygen at a level of 25±5%), with 5% $CO_2$ and 37° C. in an appropriate medium, maintaining the pH at 7.2 to 7.4. An appropriate medium is ATCC medium 1699.

For the culture 500 to 1,000 ml spinner flasks can be used with constant agitation of 25 to 30 rpm. Analogous conditions, esp. for larger cultivation facilities, can be determined by those skilled in the art, using the provided information.

Example 2

Manufacturing of a *M. hyopneumoniae* Vaccine

An *M. hyopneumoniae* vaccine, according to the present invention, can be prepared using the following procedures. A probe from a master seed of the intended *M. hyopneumoniae* strain is taken to inoculate an appropriate medium which is then scaled up to a total working volume of up to 1.000 to 5.000 liters. At each step, when the pH of the culture drops to ≤7.0, the color of the culture changes from bright red to an orange-brown. A microscopic observation for purity is performed to ensure no contaminants are present, such that the next vessel can be inoculated. The cultivation is finished when the DNA content of the fermentation fluid, as determined by e.g. fluorometry, exceeds 5,000 ng/ml. Purity of the final culture is confirmed by conducting a Gram stain and examining the culture by microscopic examination for morphological characteristics of *M. hyopneumoniae.*

Inactivation is achieved by adding 2 ml of 37% formaldehyde solution, per liter of culture under constant agitation, with a total contact time of at least 4 hours. After a minimum of four hours of total inactivation time, a sample is taken to determine the concentration of residual formaldehyde. Depending on the amount of residual formaldehyde, sodium bisulfite can be added to the inactivation vessel to neutralize the residual formaldehyde. If not added at this point, the sodium bisulfite is added to the blending vessel during the formulation of the final vaccine. Inactivation kinetics show that the product is inactivated within 2.5 hours and that for routine manufacture, an inactivation period of four hours is appropriate. After completion of inactivation and sampling, the antigen lot can be stored at 2° C. to 7° C. until needed for vaccine production.

The inactivated cultures may be concentrated up to three times by ultrafiltration using a 10,000 to 100,000 molecular weight filter cut-off. The concentration process is carried out either to obtain material with higher potency levels or smaller harvest volumes for storage purposes. Satisfactory, inactivated cultures of *M. hyopneumoniae* may be pooled at any time prior to blending.

For the blending of the final vaccine product, *M. hyopneumoniae* inactivated production cultures, sterile physiological saline solution, and 0.5% (w/v) CARBOPOL® 971P carbomer solution are aseptically transferred to a steam-sterilized blending vessel. The vaccine mixture is agitated constantly. After all components have been added, they are mixed for a minimum of 30 minutes.

Example 3

The Final *M. hyopneumoniae* Vaccine

Using the procedures of Example 2, the final *M. hyopneumoniae* vaccine composition was prepared as shown in Table 1 below.

TABLE 1

Final *M. hyopneumoniae* vaccine.

| | Substance | Quantity | Function/dose or/ml |
|---|---|---|---|
| Active substance | *Mycoplasma hyopneumoniae J*, inactivated | at least $10^3$ bacteria/ml before inactivation | Active ingredient |
| Constituents of the adjuvant | Carbomer | 0.8-1.2 mg/ml | Adjuvant |
| Constituents of the excipient | Sodium chloride sol. 0.85% in water for injection in bulk | q.s. to 1 ml/dose | Adjust antigen concentration |
| Constituents of the diluent | — | — | — |
| Constituents of the pharmaceutical form | — | — | — |

The *Mycoplasma hyopneumoniae* J strain used in this vaccine composition was originally isolated in England from lung lesions of swine that were infected with enzootic pneumonia, by Goodwin, Pomeroy, and Whittlestone prior to 1965 (see Goodwin, R. F. et al., (1965); Production of enzootic pneumonia in pigs with mycoplasma; *Vet. Rec.*, 77: 1247-1249). This strain is deposited at the American Type Culture Collection (ATCC) under no. 25934.

The final vaccine composition used for immunization in the following experiments consists of a total volume of 1 ml which is comprised of the three components in the volume proportion shown in Table 2.

TABLE 2

Proportions of components in final vaccine.

| Component | ml per dose |
|---|---|
| *M. hyopneumoniae* antigen | 0.667 ml |
| CARBOPOL ® 971P (0.5% solution) carbomer | 0.200 ml |
| Physiological saline | q.s. to 1 ml |

This vaccine composition is a rose to brown, opaque aqueous liquid. Its viscosity was determined as 6.95 cP at 25° C. whereas INGELVAC® *M. hyo* vaccine composition, as a commercially available control, gave 304.8 cP at 25° C.

Example 4

Twenty-Six Week Duration of Immunity for INGELVAC MYCOFLEX® Vaccine Composition

A vaccine composition according to the present invention and produced in accordance with the previous Example is protected under the trade name INGELVAC MYCOFLEX® vaccine composition (or alternatively INGELVAC® MycoFLEX). The following duration of immunity was observed by administration of this vaccine composition. This study was conducted to establish a 26 week duration of immunity for the new vaccine by demonstrating the efficacy and safety of the product against heterologous challenge with *M. hyopneumoniae* (*M. hyo*) at twenty-six weeks post vaccination.

Materials and Methods

A challenge study was performed following GLP guidelines. For this study male, crossbred commercial piglets that were seronegative for *M. hyo* and PRRSV antibodies were included into five treatment groups (Table 3).

TABLE 3

| | | | Group information | | | |
|---|---|---|---|---|---|---|
| Group | No. of animals | Age at vaccination | Treatment | Route administered/ dose | Challenge (Intra-tracheal) | Necropsy |
| 1 | 20 | 21 ± 5 days | INGELVAC MYCOFLEX ® | i.m., 1 ml | Study Day 184 | Study Day post challenge 33 |
| 2 | | | INGELVAC MYCOFLEX ® (safety serial) | i.m., 1 ml | | |
| 3 | | | Licensed, non-mineral-oil-adjuvant-containing vaccine against *M. hyo* | i.m., 2 ml | | |
| 4 | | | Saline placebo (challenge controls) | i.m., 1 ml | | |
| 5 | 10 | | No treatment (negative controls) | — | | No challenge |

Four out of the five groups were challenged at 26 weeks post-vaccination with a heterologous strain of virulent *M. hyo*. The animals were observed for 33 days after challenge for clinical signs. Blood samples were taken for IDEXX HERDCHECK®ELISA testing for *M. hyo* IgG antibodies throughout the study. After necropsy the lungs were extracted, scored for lesions (see Straw B. E., et al., 1986: Examination of Swine at Slaughter. Part II. Findings at Slaughter and their Significance), and samples were taken for *M. hyo* DNA detection by PCR.

Results

The primary criterion of duration of immunity at 26 weeks was the clinically relevant reduction of lung lesions by 50% after challenge with a virulent *M. hyo* isolate administered 26 weeks after vaccination. Statistically significant lower lung lesions were found in all vaccinated groups, versus the challenge control group (Table 4).

TABLE 4

Pairwise comparison results from the Wilcoxon Rank Sum Test

|  | Comparison | | |
| --- | --- | --- | --- |
|  | 1 vs 4 | 2 vs 4 | 3 vs 4 |
| p-Value | 0.0023 | 0.0031 | 0.0334 |

After challenge, a reduced presence of *M. hyo* DNA detection in the lung samples of the animals from all vaccinated groups compared to the challenge controls was detected by PCR. A statistically significant ($p \leq 0.0375$) secondary antibody immune-response was noted in all vaccinated animals after challenge on DPC (Days Post Challenge) 14 and 32. The only clinical observation in the study was coughing, which was scored first on DPC 14 and was sporadic up until the end of the study. None of the clinical signs were severe enough to be clinically relevant in any treatment group. In the seven days post vaccination observation period, neither local injection site reactions nor systemic adverse reactions were observed.

Discussion and Conclusion

Vaccinated animals (INGELVAC MYCOFLEX®, INGELVAC MYCOFLEX® [safety serial], and the licensed non-mineral-oil-adjuvant-containing vaccine against *M. hyo*) showed a clinically relevant reduction of lung lesions by 50% (for the licensed product 46%), which was statistically significant compared with the animals from the challenge control group. This reduction indicated efficacy in host animals challenged with the heterologous strain of *M. hyo* at 26 weeks after vaccination. *M. hyo* DNA detection in the lung samples were reduced in all animals vaccinated with the vaccine of the invention but not with the licensed product. Seroconversion was seen in all the vaccinated treatment groups after challenge. A statistically significant difference in post-challenge serology results (DPC 14 and 32) was noted between all vaccinated groups and the control group. There were no statistically significant differences between the vaccinated groups for any clinically relevant sign. All these findings suggest that the vaccine of the invention induces protection against *M. hyo*.

There were no local or systemic adverse reactions to the vaccine during the seven days post vaccination. High tolerance was shown for INGELVAC MYCOFLEX®, vaccine composition independent of the antigen dose applied. In conclusion, a single dose of 1 ml of INGELVAC MYCOFLEX® vaccine composition administered to pigs at about three weeks of age builds up an immunity of at least 26 weeks while showing a very good local and systemic tolerance.

Example 5

Rapid Onset of Protection of Two Weeks for a Novel One Dose *Mycoplasma* Vaccine Materials and Methods The aim of this study was to demonstrate the onset of protection for a novel inactivated *M. hyo* vaccine (INGELVAC MYCOFLEX® vaccine composition; this name first quoted in accordance with the publication; it is the same product as tested in Example 4) two weeks following vaccination in a validated pig challenge model. A total of fifty sero-negative commercial cross-bred pigs were allocated to one of the three groups according to Table 5. All pigs in groups A and B were challenged with a virulent strain of *Mycoplasma hyopneumoniae* fourteen days following vaccination. All animals were necropsied on day 42 of the study.

TABLE 5

| Study design | | | | |
| --- | --- | --- | --- | --- |
| Group | Vaccination | No | Challenge | Necropsy |
| A | INGELVAC MYCOFLEX ®* at 3-4 weeks of age (Study day 0) | 22 | Day 14 | Day 42 |
| B | No [challenge control] | 22 | Day 14 | Day 42 |
| C | No [strict control] | 6 | No | Day 42 |

The primary parameter for onset of protection was the extent of lung lesions and the extent was calculated as published by Thacker, B. et al. (see *Proc. IPVS,* 1988, p. 69). The underlying basis for this calculation is the factored weight of each lung lobe of healthy animals.

Pigs were randomized, according to initial body weight, and placed in pens containing 4 animals each, two piglets each for groups A and B. Animals in the strict control group (C) were housed separately.

The null hypothesis was that the pigs in groups A and B were equal with regard to the extent of lung lesions. Since the resulting data was not normally distributed, it was analyzed by the Wilcoxon Mann-Whitney test. The test was designed as a two tailed-test and differences were considered to be statistically significant if $p \leq 0.05$.

Results

The extent of median factored lung lesions, as measured by a factored weighed lung involvement, were significantly reduced in vaccinated animals (group A, median 0.123) as compared to challenged controls (group B, median 2.925) at day 42 (significant difference at $p \leq 0.05$). This significant difference was not only observed for the entire lung, but also for all individual lung lobes. None of the six strict control animals exhibited any lung lesions (not shown in table), which confirms the validity of the challenge model.

Discussion

For efficacious control of *M. hyo* in modern production systems it is mandatory to have a vaccination tool available with a rapid onset of protection as well as a long duration of protection. It has been previously shown by Ohnesorge and von Richthofen (2007; *Proc. APVS,* 2007, p. 294; see Example 4 of this application) that INGELVAC MYCOFLEX® has a duration of immunity of about 26 weeks. When combined with the results of this study, which clearly provides evidence for a rapid onset of protection of two weeks following vaccination, INGELVAC MYCOFLEX® offers a protection with fast onset and prolonged duration.

REFERENCES

The following references, to the extent that they provide exemplary procedural or other details supplementary to those set forth herein, are specifically incorporated herein by reference.

*Pharmeuropa*, Vol. 8, No. 2, June 1996.
Goodwin, R. F. et al., (1965); Production of enzootic pneumonia in pigs with mycoplasma; *Vet. Rec.,* 77: 1247-1249.
Straw B. E., et al., 1986: Examination of Swine at Slaughter. Part II. Findings at Slaughter and their Significance.
Thacker, B. et al., *Proc. IPVS,* 1988, p. 69.
Ohnesorge and von Richthofen, *Proc. APVS,* 2007, p. 294.

What is claimed is:

1. A method of preparing a one phase aqueous composition comprising a *Mycoplasma hyopneumoniae* bacterin, an acrylic acid polymer in a concentration range between 0.8 and 1.2 mg/ml, a pharmaceutically acceptable carrier, and substantially no oil;
   comprising:
   a. cultivating a *M. hyopneumoniae* whole cell culture such that the *Mycoplasma hyopneumoniae* bacterin has an antigen amount of at least 3 log 10 per ml;
   b. inactivating the *M. hyopneumoniae* whole cell culture;
   c. isolating an immunizing amount of a *Mycoplasma hyopneumoniae* bacterin;
   d. admixing an acrylic acid polymer in the concentration range between 0.8 and 1.2 mg/ml; and
   e. admixing a pharmaceutically acceptable carrier.

2. The method of claim 1, wherein the *M. hyopneumoniae* whole cell culture is inactivated by a method selected from the group consisting of heat denaturation, shear force, and a chemical agent.

3. The method of claim 2, wherein the chemical agent is selected from the group consisting of binary ethyleneimine (BEI) and formalin.

4. The method of claim 1, wherein the one phase, aqueous composition consists essentially of no other ingredients.

5. The method of claim 1, wherein said one phase, aqueous composition consists essentially of substantially pure formalin-inactivated whole cell *Mycoplasma hyopneumoniae* J (ATCC 25934) bacterin having an antigen amount between 5 log 10 and 8 log 10 per ml before inactivation; about 1 mg/ml carbomer; and up to 1 ml 0.85% (w/v) sodium chloride aqueous solution.

* * * * *